US008636680B2

(12) United States Patent
Hiebert (10) Patent No.: US 8,636,680 B2
(45) Date of Patent: Jan. 28, 2014

(54) SURGICAL POSITIONING SYSTEM

(71) Applicant: Eugene Lloyd Hiebert, Salem, OR (US)

(72) Inventor: Eugene Lloyd Hiebert, Salem, OR (US)

(\*) Notice: Subject to any disclaimer, the term of this patent is extended or adjusted under 35 U.S.C. 154(b) by 0 days.

(21) Appl. No.: 13/744,233

(22) Filed: Jan. 17, 2013

(65) Prior Publication Data
US 2013/0206148 A1     Aug. 15, 2013

Related U.S. Application Data

(63) Continuation of application No. 12/584,337, filed on Sep. 2, 2009, now Pat. No. 8,469,911.

(51) Int. Cl.
*A61F 5/00*     (2006.01)
(52) U.S. Cl.
USPC ............................................. 602/13; 128/845
(58) Field of Classification Search
USPC ............ 602/13; 128/845, 869–870, 874–876; 5/625, 628, 632
See application file for complete search history.

(56) References Cited

U.S. PATENT DOCUMENTS

| | | | |
|---|---|---|---|
| 3,212,497 A | 10/1965 | Dickinson | |
| 3,689,945 A | 9/1972 | Laerdal | |
| 3,762,404 A * | 10/1973 | Sakita | 602/6 |
| 4,234,982 A | 11/1980 | Bez et al. | |
| 4,657,003 A * | 4/1987 | Wirtz | 128/869 |
| 4,862,879 A | 9/1989 | Coombs | |
| 4,885,811 A | 12/1989 | Hayes | |
| 4,962,769 A | 10/1990 | Garcia | |
| 4,999,867 A | 3/1991 | Toivio et al. | |
| 5,121,756 A | 6/1992 | Koledin | |
| 5,154,185 A | 10/1992 | Latimer et al. | |
| D362,913 S | 10/1995 | Eisenberg et al. | |
| 5,586,348 A | 12/1996 | Toivio et al. | |
| 5,621,934 A | 4/1997 | Olkkonen et al. | |
| 5,626,150 A | 5/1997 | Johnson et al. | |
| 5,634,222 A | 6/1997 | Zwickey | |
| 5,647,079 A | 7/1997 | Hakamiun | |
| 5,659,908 A | 8/1997 | Nishino | |
| 5,906,205 A * | 5/1999 | Hiebert | 128/845 |
| 6,308,353 B1 | 10/2001 | Van Steenburg | |
| 6,318,372 B1 * | 11/2001 | Hiebert | 128/869 |

OTHER PUBLICATIONS

Schroer Manufacturing Company, Shor-line® catalog; "Vacu-Positioner," 3 pp., p. G1 (1987).
Schroer Manufacturing Company, Shore-line® catalog; "Vacu-Positioner," p. F20 Sep. 1998).
Natus, Olympic Papoose Boards, http://www.natus.com/index.cfm?pa . . . , 2 pp. (visited Jun. 17, 2010).
Natus, Olympic Vac-Pac, http://www.natus.com/index.cfm?pa . . . , 2 pp. (visited Jun. 17, 2010).
SW Med-Source, http://www.swmedsource.com/bean . . . , 6 pp. (visited Jun. 17, 2010).

\* cited by examiner

*Primary Examiner* — Michael A. Brown
(74) *Attorney, Agent, or Firm* — Klarquist Sparkman, LLP (57) ABSTRACT

A surgical positioning system includes a flexible air-impermeable shell filled with beads that is wrapped against the patient and subjected to a vacuum to hold the patient in place. The shell includes rounded shoulder portions, on either side of a separately inflatable pillow, to envelop portions of the patient's neck and shoulders, tapered waist portion to provide easy access to a patient's forearms and lower lateral abdomen, and expanded wrist hand portion to cradle the patient's hands and thighs.

15 Claims, 8 Drawing Sheets

SURGICAL POSITIONING SYSTEM

FIELD

This invention relates to an improved positioning system for supporting, restraining and/or immobilizing a patient during medical treatment and, more particularly, for supporting, restraining and immobilizing a patient when in a supine position during surgery.

BACKGROUND

Vacuum actuated positioning aids or devices are utilized in the operating room for positioning patients in the supine, prone and lateral positions. They are frequently used when the patient is in the lateral position, i.e., on his or her side, for a multitude of surgical procedures, such as brain, chest, kidney, shoulder and hip surgery, to name a few. The devices typically comprise a flexible air impervious bag containing small particles or beads which consolidate into a rigid mass when the bag is evacuated. See, for example, U.S. Pat. No. 3,762,404 to Sakita and U.S. Pat. No. 5,906,205 to Hiebert. Devices according to the Hiebert patent are sold by Hug-U-Vac under the trademark HUG-U-VAC®.

More specifically, devices of this type typically are filled with thousands of tiny, elastically deformable, generally spherical, polystyrene or plastic beads. When the device is in the soft (unevacuated) condition, the beads are free to move around so that the device can be molded to the patient's body. When air is removed (using a vacuum source), atmospheric pressure forces the beads together into a solid mass, positioning yet immobilizing the patient in the selected position. Allowing air back into the device returns it to its initial soft condition, ready for re-use.

These positioning devices, sometimes referred to as bean bag positioners, typically have a generally square or rectangular shape and in some cases are provided with a U-shaped shoulder cutout located centrally along one edge. One line of bean bag and "vacuum pac" positioners is offered by SW Med-Source, P.O. Box 93115, Southlake, Tex. (www.swmedsource.com). SW Med-Source offers gel bean bag positioners as well. Another line of Olympic VAC-PAC® bean bag positioners is offered by Natus Medical Incorporated, 1501 Industrial Road, San Carlos, Calif. (www.natus.com).

Fabric-style devices also are used for positioning patients during exam or treatment. These devices typically are wrapped around one or more sections of the patient, and include one or more wide canvas flaps with adjustable VELCRO™ straps. The flaps may be detached/unwrapped to allow a particular area of the patient to be selectively exposed for treatment. See, for example, Natus' OLYMPIC PAPOOSE BOARDS™ (www.natus.com)

Foam pads and other positioning aids also are used to reduce pressure points and provide patient support during surgery.

There remains however a need for an improved positioning system for surgery in which the patient is in a supine position, especially surgeries in which the patient is supported on an inclined surgery table as, for example, when the patient is in the Trendelenburg, Reverse Trendelenburg or Lateral Oblique positions.

In the Trendelenburg position, the patient is laid flat on her back with her feet above her head. This position may be used during certain laparoscopic and other procedures such as colectomies, hysterectomies, prostatectomies and robotic procedures. In some procedures, the angle of incline is so steep that the patient is in a so-called Steep Trendelenburg position. In the Reverse Trendelenburg position, the patient is tilted in the opposite direction with his head above his feet.

Accordingly, it is desirable to provide an improved positioning system for patients positioned in a supine position during surgery, especially surgeries requiring the patient to be oriented in an inclined position rather than a perfectly horizontal supine position.

It also is desirable to provide an improved positioning system for certain types of surgeries including, for example, laparatomies, laparoscopic procedures, colorectal procedures, gynecological procedures, neurological procedures, cholecystectomies, Nissin Fundoplications and da Vinci procedures.

It is further desirable to provide an improved positioning system for supine patients with better head and neck support.

SUMMARY

In one example, a surgical positioning device for positioning the body of the patient in a selected position includes a flexible and air-impermeable shell having an air-impermeable top wall joined with an air-impermeable bottom wall, the shell defining an air-impermeable outer periphery. The outer periphery of the shell includes an upper edge, a lower edge and opposing first and second lateral edges extending between the upper edge and lower edge, and defines a laterally extending midline extending between the opposing lateral edges. An upper portion of the shell extends between the laterally extending midline and the upper edge. A lower portion of the shell extends between the laterally extending midline and the lower edge. A central region for supporting the patient's torso straddles the laterally extending midline and extends between the upper portion and lower portion. The upper portion includes opposing first and second shoulder support regions positioned laterally outward of the central region and adjacent the upper edge for supporting the patient's respective shoulders.

In another example, the lower edge defines a longitudinally recessed perineal access region for providing access to the patient's perineal region.

In another example, the upper portion includes rounded shoulder portions each having a radius of curvature that generally increases as the shoulder portion extends laterally outwardly toward its respective lateral edge. The width of the device at the shoulder portions and at its widest point is such that the device may be wrapped up and partially over the shoulders and proximate to the neck of a patient lying in a supine position.

In one example, the device is filled with many small beads, allowing the device to be pliable and conform to a patient's anatomy.

In another example, the lower portion includes opposed wrist portions which project laterally outwardly near the lower edge of the device. The device has a width dimension at the wrist portions that allows the device to be wrapped upwardly to provide lateral support for a patient's hands, wrists and thighs when the patient is in a supine position.

In yet another example, the opposed lateral edges of the device include a tapered waist portion located between the wrist portions and a point proximate the midline to give the device a low profile in the vicinity of the patient's wrists, forearms and lower lateral abdomen so as to provide greater surgical access in these areas, IV access, and access for surgical instruments.

In yet another example, the upper portion provides an adjustable pillow portion to support the patient's neck and head.

A method of supporting the patient in a supine position includes positioning a flexible air-impermeable shell between a patient and a support, such as an operating table. The shell has an upper edge and a lower edge and opposing first and second lateral edges extending between the upper edge and lower edge. The shell defines a laterally extending midline extending between the opposing lateral edges, and includes first and second shoulder support regions positioned adjacent the upper edge and a longitudinally recessed perineal access region adjacent the lower edge. When the patient is in the supine position, the first and second shoulder support regions are folded upwardly to at least partially engage each of the patient's shoulders. The shell is then substantially evacuated such that the first and second shoulder support regions support and retain in place each of the patient's respective shoulders.

In another example, a method of supporting a patient includes urging first and second upper arm support regions of the shell to at least partially engage each of the patient's respective upper arms, such that when the shell is evacuated the first and second upper arm support regions at least partially matingly engage each of the patient's upper arms.

In a further example, a method of supporting a patient includes adjustably inflating the pillow portion to provide appropriate support for the patient's head and neck.

The foregoing and other objects, features and advantages of the invention will become more apparent from the following detailed description, which proceeds with reference to the accompanying figures.

DETAILED DESCRIPTION

Figure 1:
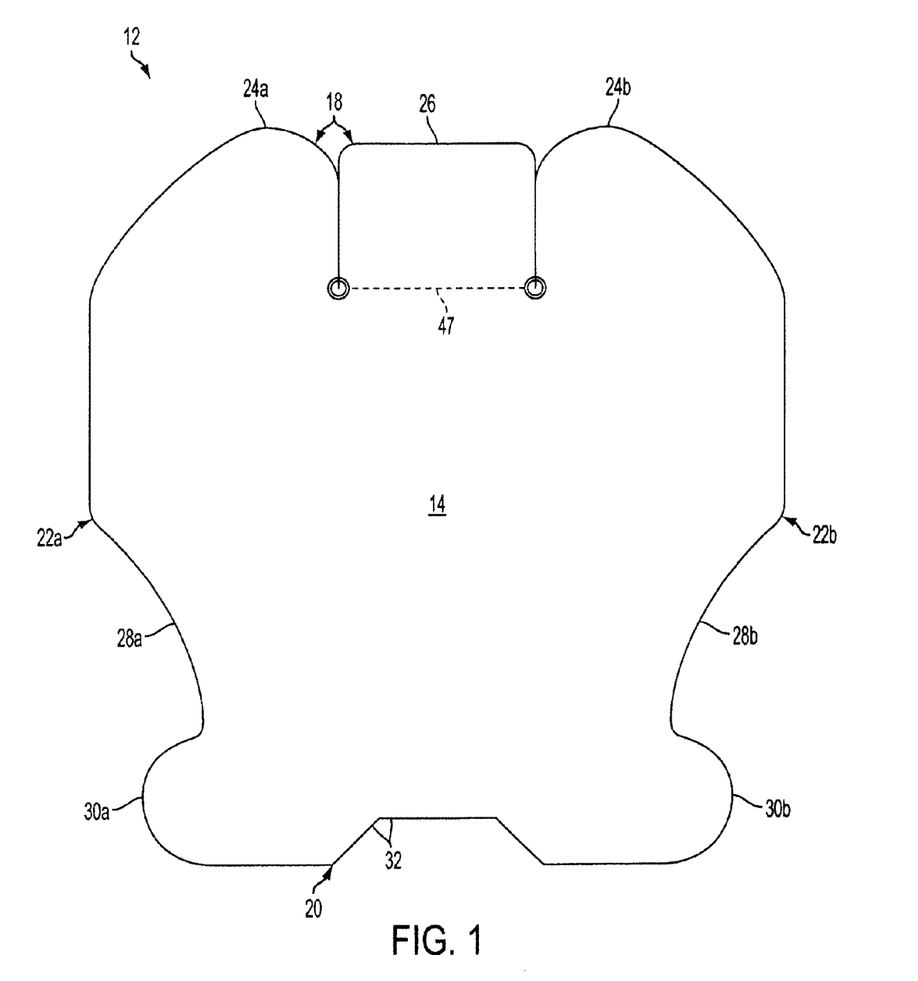
FIG. 1 is a top plan view of one embodiment of the present invention.
Figure 2:
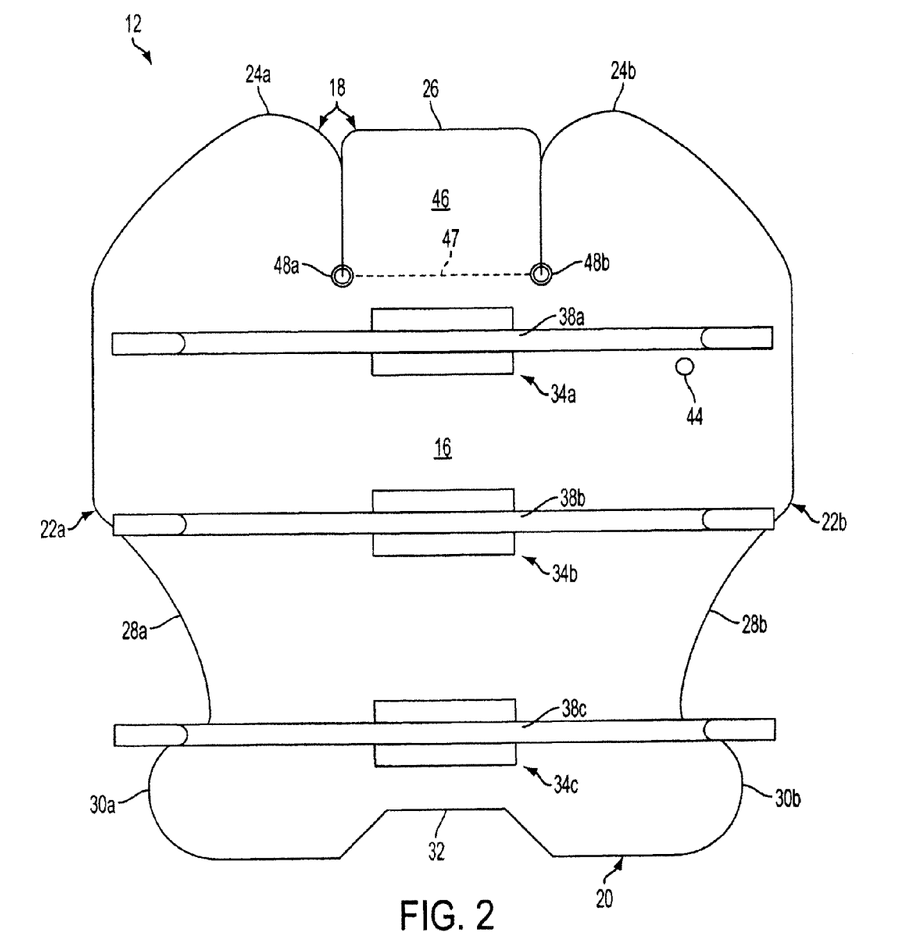
FIG. 2 is a bottom plan view of the embodiment of FIG. 1.

Referring to FIGS. 1 and 2, a surgical positioning system described herein includes a generally flat bag 12 fabricated of flexible, air impermeable material. The bag preferably is about 1½ to 2½ inches thick. One suitable material is "Rocheux Supreme" polyvinyl waterbed film, distributed by Rocheux International, Inc., Carson, Calif., although other materials having similar physical properties may be used. The Rocheux material has desirable low temperature, tear, heat sealing and flexing qualities, as well as superior hydrostatic resistance which makes it particularly suitable for the present positioning system. It also has good resilience, returning quickly to its prior conformation, thereby holding the patient more securely. It is mildew-, bacteria-, puncture- and fire-resistant. Its physical properties are specifically as follows:

| | | |
|---|---|---|
| Thickness (inches) | 0.024, +5%, −0 | ASTM D-751 |
| Embossing | Plain | |
| Weight (oz./yd.$^2$) | 17.5 (min.) | ASTM D-751 |
| Volatility (% loss) | 1.5 (max) | ASTM D-1203-86, Method B |
| Elongation (%) | 350-360 (min) | ASTM D-882 |
| Elongate change after 14 days × 150° F. (%) | Less than 10 | ASTM D-882 |
| Breaking strength factor (psi) | 44 | ASTM D-882 |
| Tensile change after 14 days × 150° F. (%) | Less than 10 | ASTM D-882 |
| Graves tear (lbs.) | 5.6 (min) | ASTM D-1004 |
| Low temperature (° F.) | −20 (min) | ASTM D-1790 |
| Dimensional stability (%) | −5 (max) | ASTM D-1204 |
| Specific gravity | 1.21-1.23 | ASTM D-792 |
| Mildew resistance | Passes ATCC No. 6275 | California Bureau of Home Furnishings, Bulletin 128 |
| Bacteria resistance | Passes ATCC No. 6538, 4352 | California Bureau of Home Furnishings, Bulletin 128 |
| Hydraulic resistance (psi) | 75 | ASTM D-75 1 |
| Puncture resistance (lbs.) | 34.3 | California Bureau of Home Furnishings, Bulletin 100 |

Figure 4:
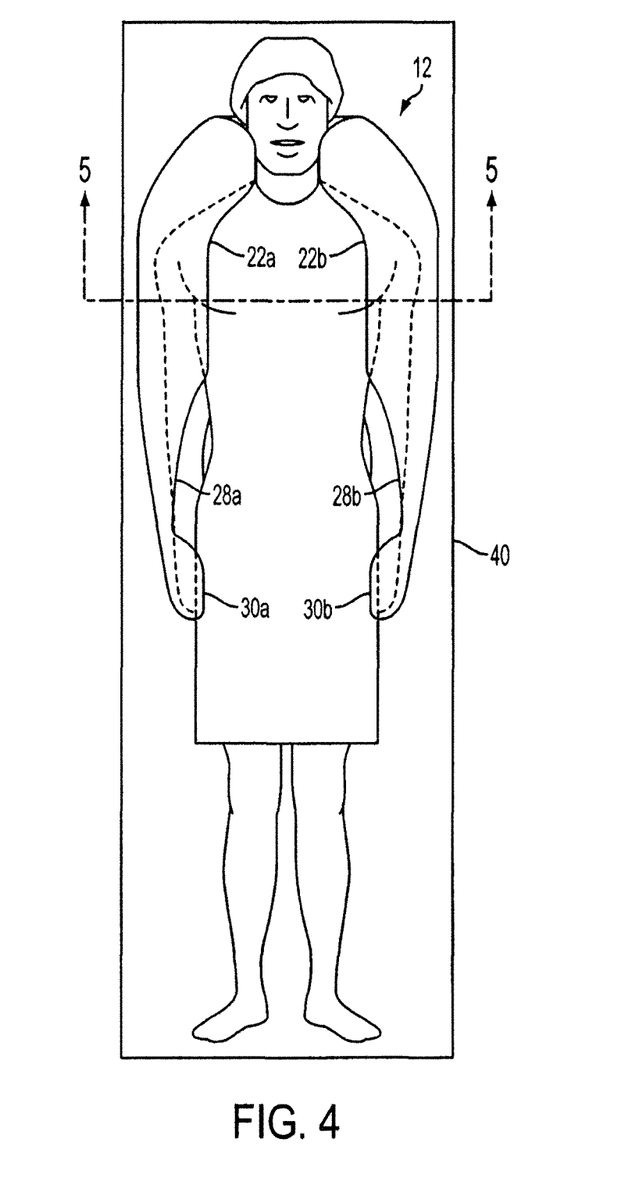
FIG. 4 is a top plan view of the FIG. 1 embodiment, patient and operating table.

The bag 12 includes top and bottom opposing walls 14, 16 which are radio frequency welded, heat sealed or otherwise joined together at their upper, lower and lateral edges 18, 20, 22 for strength and airtightness. The bag's preferred width at its widest point is about 42 inches, which exceeds the shoulder width of most patients. The bag's preferred length at its longest point is about 46 inches, which corresponds generally to the distance between the neck and upper thighs of an average height patient. Thus, when the patient is placed in the supine position on the bag 12, as shown in FIG. 4, the lateral edges 22 can be folded up along the patient's neck, shoulders, arms, hips and upper thighs and packed snuggly against the patient's body to accommodate the natural contours thereof.

Referring again to FIGS. 1 and 2, the upper edge 18 includes two opposed shoulder edge portions 24a, 24b, and a pillow edge portion 26 located therebetween. Adjacent to the pillow edge portion 26, the shoulder edge portions 24a, 24b have a relatively tight radius of curvature, preferably about 4⅜ inch, allowing the upper edge 18 to be folded upwardly adjacent either side of the patient's head and neck for support. As upper edge 18 extends laterally outwardly toward edges 22, the upper edge retains an arc-like curvature but the radius of curvature of shoulder edge portions 24a, 24b increases significantly, preferably to about 22 to 23 inches, to expand the width of the bag and allow the upper edge (when folded) to wrap around and at least partially overlie the patient's shoulders to support and immobilize the patient's upper body. The shoulder portions 24a, 24b of the upper edge 18 terminate where lateral edges 22a, 22b begin, defining the widest point of the bag.

Lateral edges 22a, 22b each define opposed cut out portions 28a, 28b, and opposed projecting wrist supporting portions 30a, 30b. Wrist supporting portions 30a, 30b project outwardly to increase the width of the bag in the region proximate the lower edge 20. The width of the bag across the wrist supporting portions preferably is about 35 inches. The wrist supporting portions may be folded upwardly to provide lateral support for the patient's wrists and hands. They help secure the patient's wrists and hands against the side of the patient's body. The cut out portions 28a, 28b give the bag a tapered waist and low profile in the vicinity of the patient's arms so as to provide easy access to the patient's wrists and forearms for insertion of an IV, surgical access to the lower lateral abdomen, access for surgical instruments and other purposes.

The lower edge 20 preferably includes a central trapezoid-like cut out 32 to provide perineal access. The cut out 32 preferably conforms to perineal access cut outs sometimes used in operating room table designs to provide access for speculums, rectal instruments and the like.

As shown in FIG. 2, a plurality of strap patches 34a, 34b, 34c (three shown) are secured by heat sealing, radio frequency welding or otherwise to the bottom wall 16. The patches preferably are centered and spaced apart along the bag's longitudinal centerline/axis. Before the strap patches are attached to the bottom wall, an elongate fastener strap 38a, 38b, 38c, is attached, preferably by sewing or other fixed attachment method, to each patch 34a, 34b, 34c. FIG. 2 shows the ends of each strap doubled back on each other for purposes of illustration. The fastener straps 38a, 38b, 38c (FIGS. 7, 8) secure the bag 12 to an operating table 40 (FIG. 4) on which the bag and patient are supported. Each strap has a fastening means to fasten one end of the strap to the other or, when looped around an anchor, to itself to safely secure the bag 12 to the operating table and thereby prevent the bag from sliding relative to the operating table. The fastening means preferably includes Velcro® brand hook-and-loop fastening means or equivalent hook-and-loop fasteners, although adjustable buckle style, clip and other tie down straps will suffice. More specifically, each end of the straps may be looped around an operating table side rail, D-ring or other anchor structure on the table 40, and then secured back to itself using hook-and-loop fasteners or other fastening means. Alternatively, the two ends of each strap may be secured to one another along the underside of the operating table 40, depending on the design of the table.

It will be appreciated that once the straps are secured to the operating table, the fixed attachment of the straps to the strap patches 34a, 34b, 34c (and effectively to the bag 12 as well), keep the bag from sliding laterally on the operating table as, for example, when the table is tilted laterally to place the patient in the Trendelenburg and Lateral Oblique position.

Figure 5:
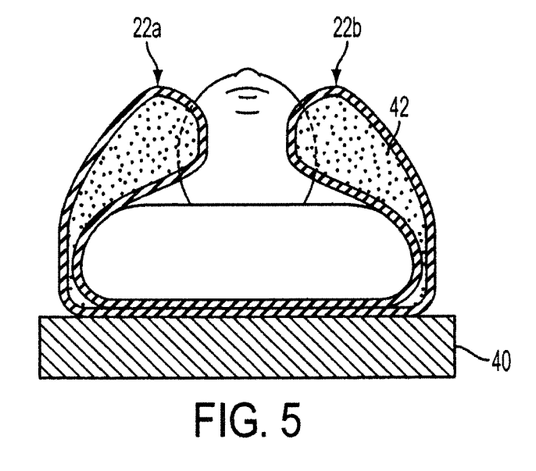
FIG. 5 is a sectional view taken along line 5-5 in FIG. 4.

Before walls 14, 16 are joined together to form the enclosed bag 12, the bag is filled with a charge of elastically deformable plastic beads 42 (FIG. 5). The beads preferably are made of expanded plastic materials, such as polystyrene or polyvinyl chloride, because of their high mechanical strength, elastic deformability and low specific gravity. Beads 42 of expanded polystyrene are especially preferred. When the bag 12 is in the unevacuated condition, the beads 42 remain loose within the bag such that the upper, lower and lateral edges of the bag can be easily moved or folded up along the side of the patient's neck, shoulder, arms, hips and upper thighs to cradle and support the patient in the selected position. The bag preferably is configured to wrap around and overlie at least a portion of the patient's shoulders and upper chest, as shown in FIG. 4.

Figure 6:
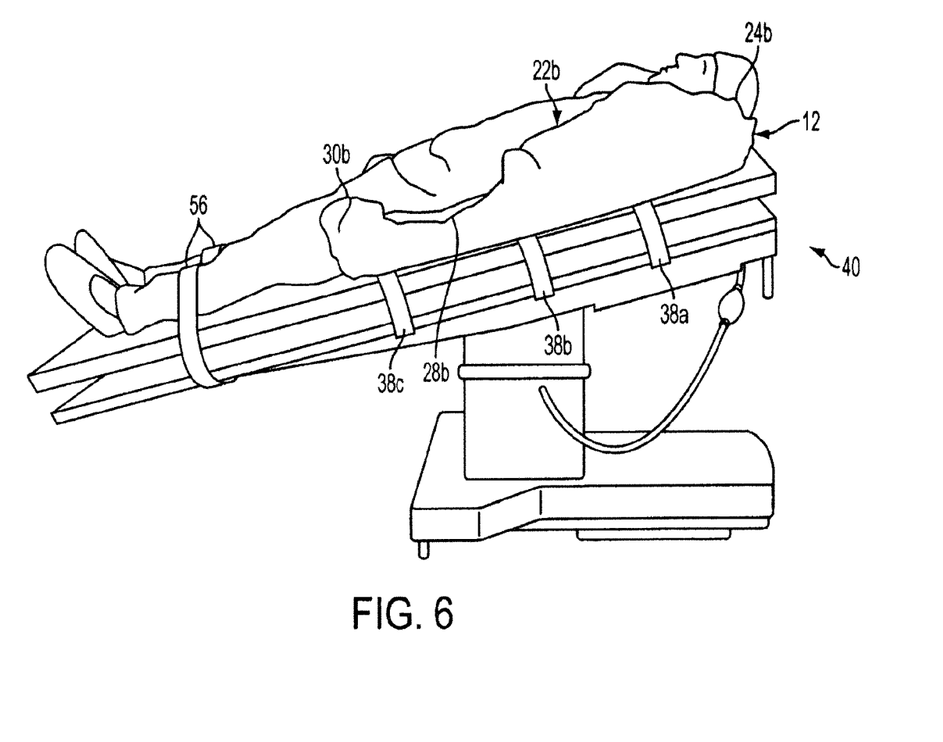
FIG. 6 is a perspective view of the FIG. 1 embodiment and showing a patient in the Reverse Trendelenburg position.
Figure 7:
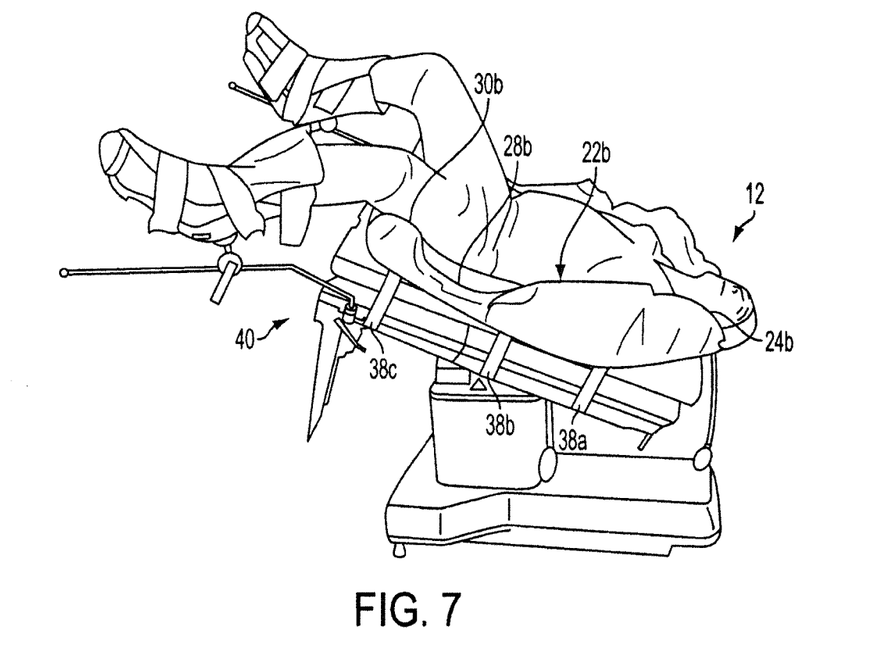
FIG. 7 is a perspective view of the FIG. 1 embodiment and showing a patient in the Trendelenburg as well as Lateral Oblique position.

The bottom wall 16 of the bag 12 is provided with a valve 44 (FIG. 2) which communicates with the interior of the bag for evacuating air therefrom. The valve 44 may be identical or similar to the one described in U.S. Pat. No. 5,906,205, the disclosure of which is herein incorporated by reference. The valve may have a male portion with a protruding valve stem and a plastic tube which connects the valve stem to the bottom wall 16 in an airtight manner. The valve also preferably includes a female portion that may be releasably placed over the male portion to depress the valve stem and open the valve to allow ingress or egress of air. When a source of vacuum is attached to the female portion, air is withdrawn from the interior of the bag. This causes the plastic beads 42 to be packed (or to congregate) into a tight configuration, conforming to the patient's body, as shown in FIGS. 6 and 7. When the female portion is removed from the male portion, the valve closes and no air can enter or exit the bag, thereby maintaining the conformity of the bag to the patient's body. When the patient is to be released, the female portion of the valve 44 (without the vacuum hose attached) is placed over the male portion. This opens the valve 44, thereby allowing air to enter the bag and loosening the configuration of the beads so that they reside in a more relaxed, fluid state. This allows the bag to flatten. It will be appreciated that a variety of conventional valves can be used to withdraw air from the bag, maintain the bag in an evacuated state and allow air to reenter the bag.

Figure 3:
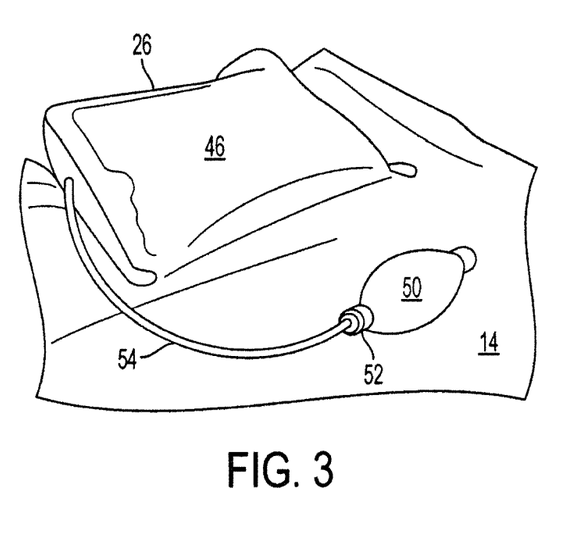
FIG. 3 is a perspective view of one portion of the FIG. 1 embodiment.

As shown in FIGS. 1, 2 and 3, the bag 12 includes an inflatable pillow 46 which is attached to a cut out portion in the bag located centrally along upper edge 18 between shoulder edge portions 24a, 24b. There is no fluid communication between the interiors of the bag 12 and pillow 46, each of which constitutes an air impermeable compartment of its own. The pillow has a width of about 12 inches in one embodiment of the present positioning system.

As shown best in FIG. 3, the pillow 46 is connected to the bag 12 along a hinge line 47 extending between reinforcement grommets 48a, 48b (FIGS. 1, 2), which preferably is formed by joining the top and bottom walls 14, 16 by heat sealing, radio frequency welding or otherwise. The pillow is free to pivot about the hinge line 47 toward the top wall or bottom wall. The pillow 46 provides support for the patient's head and neck, and may be inflated more or less based on the desired position and orientation for the patient's neck/head during the particular procedure, patient's anatomy and other factors. The pillow may be flipped forward to rest on the top wall 14 to accommodate shorter patients.

The pillow preferably is made of the same material as the bag 12 itself. The pillow may be inflated by a number of conventional techniques, one of which is a hand held inflation bulb 50 (FIG. 3) having a release valve 52 attached to a length of plastic tubing 54 in air-type fluid communication with the interior of the pillow.[1]

[1] It will be appreciated that the pillow 46 provides independently adjustable support for the patient's head and neck, allowing the surgeon or nurse to adjust the firmness of the support as well as the position and orientation of the patient's head and neck.

Figure 8:
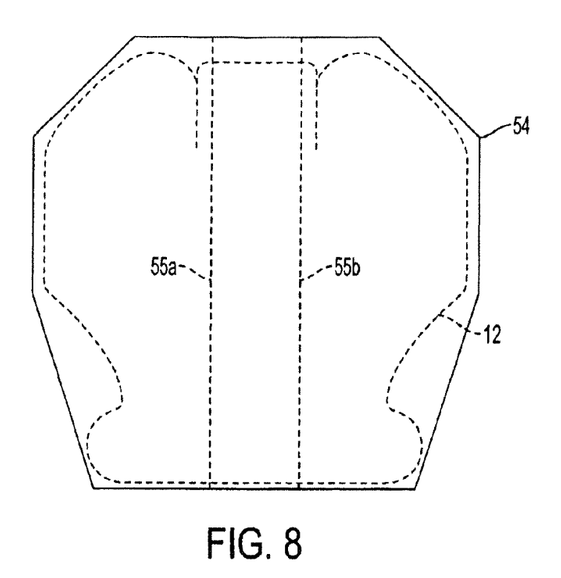
FIG. 8 is a top plan view of a slipcover used in conjunction with the FIG. 1 embodiment.

Referring to FIG. 8, the present positioning system may be provided with a disposable, waterproof slipcover 54 having a size and shape compatible with covering the top wall 14 of the bag 12, a top layer for fully covering the top wall 14 and bottom layer for partially covering the bottom wall 16. The slipcover 54 is provided with slits 54a, 54b that provide side pocket openings in the bottom layer of the slipcover, similar to a throw pillow cover. The openings or pockets allow the sides of the bag to be slipped into the slipcover side pockets such that the top layer of the slipcover covers the top surface of the bag.

Figure 9:
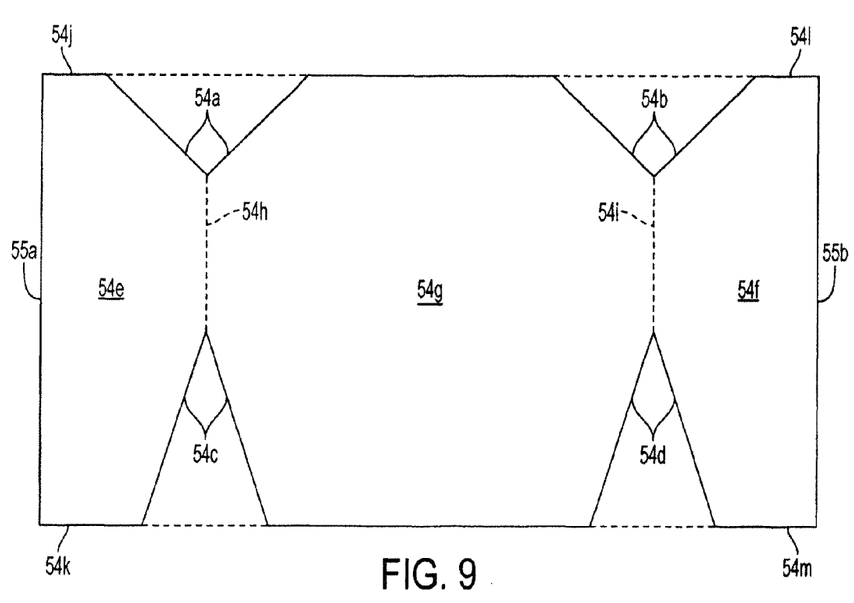
FIG. 9 illustrates a method of forming a slipcover.

With reference to FIG. 9, the slipcover is formed from a rectangular piece of fabric or material that is cut along cut lines 54a, 54b, 54c, 54d, defining side panels 54e, 54f and central panel 54g. Panels 54e, 54f are then folded underneath central panel 54g along fold lines 54h, 54i, and the edges 54a, edges 54b, edges 54c, and edges 54d are each preferably heat sealed together to create the design shown in FIG. 8. In this way, the panels 54e, 54f form a pair of laterally opposed, two-layer side pockets with respective portions of central panel 54g.

FIG. 4 is a top plan view showing the positioning system supporting the patient in a horizontal position on the operating table 40 during surgery. Air has been evacuated from the bag 12. The positioning system 40 covers the patient's shoulders and provides lateral stabilizing support for the patient's head and neck. Lateral support also is provided for the patient's upper arms, hips and upper thighs, while still providing easy access to the patient's forearms, wrist, and lower lateral abdomen. The pillow 46 supports and orients the back of the patient's head and neck.

FIG. 5 is a transverse sectional view of the positioning system, also in the evacuated condition, taken across the patient's shoulders and upper chest. The positioning system envelopes the patient's upper arms and a portion of the patient's upper chest while providing malleable, comfortable underlying support for the patient's posterior. The positioning system readily conforms to the patient's anatomy.

FIG. 6 is a side elevation view showing an evacuated bag 12, operating table 40 and supine patient in a Reverse Trendelenburg position, with the patient's head elevated above the feet. The patient's lower legs typically are secured to the table by one or more straps. The bag, which conforms closely to the patient's anatomy, cooperates with the straps to comfortably immobilize the patient and resist the force of gravity urging the patient to slide downwardly feet first. A foot board optionally may be placed adjacent the patient's feet. The positioning system partially envelops the patient and creates a friction contact with the patient that must be overcome before the patient may slide relative to the bag and operating table (which are effectively locked together by the straps 38a, 38b, 38c). The conformity of the bag to the contours of the patient's body helps keep the patient from sliding. The wrist supporting portions 30a, 30b, when folded up, support the patient's hands and wrists and also help create a narrow channel in the area of the patient's hips, which is typically smaller than the width of the patient's shoulders, thereby resisting any tendency of the patient to slide down the inclined plane formed by the operating table.

FIG. 7 is a side elevation view showing an evacuated bag 12, operating table 40 and supine patient in a Steep Trendelenburg position, with the patient's feet elevated above her head, and also in a Lateral Oblique position, with the patient tilted laterally to one side. FIG. 7 also depicts the patient with her legs slightly bent and feet spaced apart for certain types of gynecological, laparoscopic, abdominal and urological procedures. It will be apparent that with the patient so positioned the tendency of gravity is to cause the patient to slide downwardly head first on the table and toward one side of the table.

The positioning system envelops the patient's shoulders and a portion of her chest, creating a narrow channel around the patient's neck and shoulders to resist the tendency of the patient to slide either laterally or longitudinally on the inclined plane formed by the operating table. The system provides substantial bulk and mass in the area of the patient's shoulders to help hold the patient in place. The system's conformity to the patient's anatomy (lower back, spine, shoulder blades, etc.) contributes to hold the patient in place.

In using the surgical positioning system, the bag 12 is centered on the operating table 40, with the pillow 46 toward the head of the operating table, and securely fastened to the table using the fastening straps 38a, 38b, 38c. The straps may be secured to the side rails of the operating table. The bag is then smoothed out so that the internal beads 42 inside are evenly distributed. The disposable waterproof slipcover 54 is then placed over the bag 12 and tucked underneath.

The patient is then placed in the supine position on the bag with the neck and head resting on the pillow 46. In the case of smaller or shorter patients, the pillow can be folded forward before the patient is placed in position. The inflation bulb 50 is then used to inflate the pillow as much as necessary to support and position the patient's head/neck, typically in a neutral position for most surgeries.

The lateral sides of the bag are then folded upwardly to engage the sides, shoulders and upper arms, forearms and wrists of the patient. The lateral and superior sides are snugly packed against the patient to accommodate the natural contours thereof and provide a generally U-shaped cradle for the patient. The top of the bag conforms to the patient's posterior. While holding the patient and bag in the desired position, air is evacuated from the interior of the bag 12. Specifically, the female portion of the evacuation valve 44 is attached to the male portion and a vacuum source is connected to the end of the female portion to evacuate air from the interior of the bag. Evacuation is continued until the bag is firm to provide contoured support for the patient. When the desired level of support is achieved, the female portion is detached from the male portion and the vacuum source is detached from the female portion. The bag retains its conforming shape. It will be appreciated that many types of known valve/hose constructions can be used to create and release the vacuum.

Once the patient is secured, the operating table 40 may be inclined to place the patient in the Steep Trendelenburg, Reverse Trendelenburg, Oblique Lateral or other inclined position for surgery. The positioning system uses different techniques to immobilize the patient in a comfortable manner while avoiding the application of significant local pressure to any specific region. The system spreads the cradling/supporting force over a relatively wide surface area of the patient's anatomy and yet provides easy access to a large surface area of the patient's anatomy, including the patient's forearms and lower lateral abdomen. Significantly, the system retains the patient in place by engaging a wide surface area of the patient in a way that eliminates pressure points. The bag's low profile in the vicinity of the patient's forearms also allows surgical instruments to swing lower along the side of the patient and allows the tips of medical instruments in the abdomen to reach the inner aspect of the anterior abdominal wall with less interference from the side restraints of conventional systems. Yet, the positioning system maintains contact with a sizable surface area of the patient's anatomy, including the patient's shoulders, upper arms, forearms, hands, hips and thighs. Such surface contact provides a friction surface and contour fit to resist the tendency of the patient to slip or slide longitudinally relative to the bag.

The bag's overall design also provides protuberances or abutments that serve as longitudinal obstructions for portions of the patient's anatomy. These obstructions resist the gravity influenced tendency of the patient to slide or slip on the inclined operating table. For example, as shown in FIG. 7, the shoulder edge portions of the bag provide a longitudinal and lateral barrier for the shoulders of a patient subject to a gravitational force urging the patient to slide head first or laterally off the operating table. The wrist supporting portions restrain the patient's hands and arms from moving laterally relative to the operating table. As shown in FIG. 6, the wrist supporting portions/projections, when folded up, provide a longitudinal and lateral obstruction for the arms of a patient subject to a gravitational force urging the patient to slide feet first or laterally off the operating table. In this case, the bag 12 also cooperates with leg straps 56, which typically are used to secure the patient's lower legs to the operating table.

The bag also is designed to create narrow channels to resist sliding movement of the patient relative to the bag and the operating table. More specifically, as shown best in FIGS. 4 and 7, the bag defines a relatively narrow channel at the end where the patient's head is placed. The patient's shoulders, chest, and hips have a width dimension that exceeds the width of the head/neck channel associated with the pillow 46. Thus, when the patient is inclined head first, the narrow channel defined at the head end of the bag prevents the wider portions of the patient's anatomy from sliding longitudinally through the channel. The channel effect and shoulder wrap secures the patient even in the steepest Trendelenburg position. In addition, the wrist supporting portions 30a, 30b also define a narrowing channel in the vicinity of the patient's hands and upper thighs. For a patient to slide feet first on the operating table relative to the bag, the patient's hips and shoulders, which are wider than the wrist channel, would have to slide through the narrow channel.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A surgical positioning device for positioning the body of a patient, the device comprising:
    a flexible, air-impermeable shell having a top wall and bottom wall joined at an outer periphery, the outer periphery having an upper edge, lower edge and opposing lateral edges extending between the upper and lower edges;
    a plurality of beads positioned within the shell;
    the shell having opposed shoulder portions adjacent to the lateral edges and the upper edge, the shoulder portions having dimensions sufficient to be wrapped over and at least partially engage a patient's shoulders, the upper edge adjacent each shoulder portion being at least partially arcuate;
    the shell having opposed, laterally projecting, lower protuberances along the lateral edges proximate to the lower edge, and opposed waist portions located between the lower protuberances and shoulder portions, the waist portions together defining a transverse width between the lateral edges that is less than a transverse width between the lateral edges at the shoulder portions and less than a transverse width between the lateral edges at the lower protuberances.

2. The positioning device of claim 1, wherein the upper edge defines a recessed region between the opposed shoulder portions.

3. The positioning device of claim 1, wherein the lower edge defines a recessed region between the opposed lower protuberances.

4. The positioning device of claim 1, further comprising a valve for evacuating air from within the shell.

5. The positioning device of claim 1, further including a plurality of fastener straps fixedly secured to the bottom wall of the positioning device.

6. The positioning device of claim 5, wherein each fastener strap is secured to the bottom wall by an intermediate component.

7. The positioning device of claim 1, wherein each shoulder support portion adjoins a portion of the upper edge and a corresponding one of the lateral edges.

8. The positioning device of claim 1, wherein each shoulder support portion defines a respective arcuate portion of the upper edge.

9. A surgical positioning device for positioning a body of a patient, the device comprising:
    a flexible, air-impermeable shell having a top wall and bottom wall joined at an outer periphery, the outer periphery having an upper edge, lower edge and opposing lateral edges extending between the upper and lower edges;
    a plurality of beads positioned within the shell;
    the shell having a lower wrist engaging portion, an upper shoulder and arm engaging portions, and a waist portion therebetween;
    the waist portion having a variable waist width including a minimum waist width, the lower wrist engaging portion including opposed protuberances proximate to the lower edge and having a wrist engaging portion width greater than the minimum waist width, the upper shoulder and arm engaging portion having a shoulder width greater than the minimum waist width and extending lengthwise beyond where a patient's shoulders would be positioned;
    whereby when a patient is positioned on the device with the patient's arms against the patient's torso, the upper shoulder and arm engaging portion can be wrapped upwardly against and over the patient's upper arms and over the top of the patient's shoulders, and the wrist engaging portion can be wrapped up against and over the patient's wrists or hands, with the patient's forearms in the area of the waist portion being uncovered and accessible to medical personnel.

10. The positioning device of claim 9, wherein the lower edge includes a central recess.

11. The positioning device of claim 9, wherein the upper shoulder and arm portion includes opposed shoulder sections separated from one another.

12. The positioning device of claim 11, wherein the shell includes a neck supporting section that substantially fills the area between the opposed shoulder sections.

13. A method of positioning the body of a patient in a selected position with a surgical positioning device, the method comprising:
    positioning a flexible, air-impermeable, and bead-filled shell between a patient and a support, wherein the shell has an upper edge and a lower edge and opposing first and second lateral edges extending between the upper edge and the lower edge, wherein the shell further defines first and second shoulder support regions positioned along the upper edge, a recessed perineal access region along the lower edge, and first and second recessed waist portions along the lateral edges;
    causing the first and the second shoulder support regions to be positioned at least partially around the patient's shoulders; and
    evacuating air from within the shell such that the first and the second shoulder support regions engage each of the patient's respective shoulders.

14. The method of claim 13, wherein the shell comprises opposing lower protuberances between the recessed waist portions and the lower edge, and the method further comprises causing the lower protuberances to be positioned at least partially around the patient's arms or hands, and wherein evacuating air from within the shell causes the lower protuberances to engage the patient's arms or hands.

15. The method of claim 13, wherein a lower surface of the shell is coupled to at least one strap, and wherein the method further comprises fastening the shell to the support using the at least one strap prior to positioning the shell between the patient and the support.

* * * * *